United States Patent
Bauer

(10) Patent No.: US 9,829,394 B2
(45) Date of Patent: Nov. 28, 2017

(54) METHOD FOR DETERMINING THE FUEL TEMPERATURE

(71) Applicant: Continental Automotive GmbH, Hannover (DE)

(72) Inventor: Christian Bauer, Treffelstein (DE)

(73) Assignee: CONTINENTAL AUTOMOTIVE GMBH, Hanover (DE)

( * ) Notice: Subject to any disclaimer, the term of this patent is extended or adjusted under 35 U.S.C. 154(b) by 302 days.

(21) Appl. No.: 14/762,645

(22) PCT Filed: Dec. 11, 2013

(86) PCT No.: PCT/EP2013/076241
§ 371 (c)(1),
(2) Date: Jul. 22, 2015

(87) PCT Pub. No.: WO2014/117897
PCT Pub. Date: Aug. 7, 2014

(65) Prior Publication Data
US 2015/0362382 A1    Dec. 17, 2015

(30) Foreign Application Priority Data
Feb. 4, 2013   (DE) .................. 10 2013 201 780

(51) Int. Cl.
| | |
|---|---|
| F02M 51/06 | (2006.01) |
| G01K 11/26 | (2006.01) |
| F02M 63/00 | (2006.01) |
| F02D 41/20 | (2006.01) |
| F02M 57/00 | (2006.01) |
| G01K 13/02 | (2006.01) |
| G01N 33/22 | (2006.01) |
| F02M 47/02 | (2006.01) |
| F02D 41/22 | (2006.01) |

(52) U.S. Cl.
CPC .......... *G01K 11/26* (2013.01); *F02D 41/2096* (2013.01); *F02M 57/005* (2013.01);
(Continued)

(58) Field of Classification Search
CPC .. G01K 11/26; G01K 13/02; G01K 2013/026; G01N 33/02; F02M 63/0026;
(Continued)

(56) References Cited

U.S. PATENT DOCUMENTS

| | | | |
|---|---|---|---|
| 6,712,047 B2 | 3/2004 | Rueger | 123/479 |
| 7,110,875 B2 | 9/2006 | Fritsch et al. | 701/104 |

(Continued)

FOREIGN PATENT DOCUMENTS

| | | | | |
|---|---|---|---|---|
| DE | 10014737 A1 | 10/2001 | ............. | F02D 41/20 |
| DE | 10301264 A1 | 8/2004 | ............. | F02D 41/38 |

(Continued)

OTHER PUBLICATIONS

Korean Office Action, Application No. 20157023243, 3 pages, dated Nov. 23, 2016.
(Continued)

*Primary Examiner* — Hai Huynh
(74) *Attorney, Agent, or Firm* — Slayden Grubert Beard PLLC

(57) ABSTRACT

A method is provided for determining the fuel temperature in the high-pressure zone of a fuel injection system of a motor vehicle. The fuel injection system has at least one injector operated by a servo valve which is actuated by means of a piezo actuator. After an injection process has been carried out, the piezo actuator is discharged after the injection has ended in such a way that the servo valve can close, but a non-positive connection remains between the piezo actuator and the servo valve. This condition of reduced charge is maintained. The pressure oscillation of the actuator voltage resulting from this is recorded and from this the hydraulic natural frequency of the enclosed high-pressure volume of fuel is deduced. The prevailing fuel temperature can be determined from the natural frequency.

11 Claims, 2 Drawing Sheets

(52) U.S. Cl.
CPC ......... *F02M 63/0026* (2013.01); *G01K 13/02* (2013.01); *G01N 33/22* (2013.01); *F02D 41/222* (2013.01); *F02D 2200/0608* (2013.01); *F02D 2250/04* (2013.01); *F02M 47/027* (2013.01); *G01K 2013/026* (2013.01)

(58) Field of Classification Search
CPC  F02M 57/005; F02M 47/027; F02D 41/2096; F02D 41/222; F02D 2250/04; F02D 2200/0606; F02D 2200/0608
USPC .................. 123/490, 456; 73/114.38, 114.43
See application file for complete search history.

(56) References Cited

U.S. PATENT DOCUMENTS

| | | | | |
|---|---|---|---|---|
| 8,042,384 | B2 * | 10/2011 | Bailey | ................. F02D 19/0628 73/114.38 |
| 2011/0000465 | A1 | 1/2011 | Stoecklein et al. | ........... 123/478 |
| 2012/0020384 | A1 | 1/2012 | Mikami | ........................ 374/144 |

FOREIGN PATENT DOCUMENTS

| | | | | |
|---|---|---|---|---|
| DE | 102005036190 A1 | 2/2007 | ............. | F02D 41/20 |
| DE | 102009003279 A1 | 11/2010 | ............. | F02D 41/00 |
| DE | 102011075947 A1 | 11/2012 | ............. | F02D 41/38 |
| EP | 0995899 A2 | 4/2000 | ............. | F02D 41/20 |
| JP | 2007303395 A | 11/2007 | ............. | F02D 45/00 |
| JP | 2012026343 A | 2/2012 | ............. | F02D 45/00 |
| KR | 20010008767 A | 2/2001 | ............. | F02D 41/40 |
| WO | 2014/117897 A1 | 8/2014 | ............. | F02D 41/20 |

OTHER PUBLICATIONS

German Office Action, Application No. 102013201780.4, 4 pages, dated Aug. 9, 2013.
International Search Report and Written Opinion, Application No. PCT/EP2013/076241, 22 pages, dated Mar. 12, 2014.

* cited by examiner

METHOD FOR DETERMINING THE FUEL TEMPERATURE

CROSS-REFERENCE TO RELATED APPLICATIONS

This application is a U.S. National Stage Application of International Application No. PCT/EP2013/076241 filed Dec. 11, 2013, which designates the United States of America, and claims priority to DE Application No. 10 2013 201 780.4 filed Feb. 4, 2013, the contents of which are hereby incorporated by reference in their entirety.

TECHNICAL FIELD

The present invention relates to a method for determining the fuel temperature in the high-pressure zone of a fuel injection system of a motor vehicle which has at least one injector which is operated by means of a servo valve which is actuated by means of a piezo actuator.

BACKGROUND

As a result of ever more stringent emission regulations and increased comfort requirements, the demands made of motor vehicles, in particular their injection systems, are rising continuously, specifically in the case of diesel engines. These stringent demands (efficiency, noise etc.) can be satisfied to a greater degree on the basis of better knowledge of the precise state of the system. It is then possible to react to changing conditions, for example the changing pressure or the changing temperature of the fuel, in such a way that disruptive influences are compensated. The knowledge of the fuel temperature in the high-pressure zone of the injection system is such a relevant variable, knowledge of which gives rise to better regulation of the pressure in the high-pressure zone of the injection system as well as to more precise metering of the injected quantity of fuel.

The aspects indicated above are relevant, in particular, for the fuel injection systems of diesel engines in which the fuel pressure and the fuel temperature in the rail have to be measured or monitored in order to achieve precise metering of the injected quantity of fuel. In this context, up to now either the temperature of the fuel in the high-pressure zone has been measured directly by means of a separate temperature sensor or the temperature has been calculated by means of modeling implemented with software.

SUMMARY

One embodiment provides a method for determining the fuel temperature in the high-pressure zone of a fuel injection system of a motor vehicle having at least one injector operated by a servo valve that is actuated by a piezo actuator, the method comprising: determining a reference fuel temperature having an associated reference natural frequency of the enclosed high-pressure volume of fuel of the fuel injection system; performing an injection, and after the injection, discharging the piezo actuator to a state of reduced charge in which the servo valve is allowed to close but a non-positive connection remains between the piezo actuator and the servo valve; maintaining the state of reduced charge and determining a natural frequency of the enclosed high-pressure volume of fuel; comparing the determined natural frequency with the reference natural frequency; and determining a fuel temperature based on the comparison.

In a further embodiment, the natural frequency of the enclosed high-pressure volume of fuel is determined from the oscillation of the post-stroke voltage of the piezo actuator.

In a further embodiment, the reference fuel temperature is determined using at least one temperature sensor of the motor vehicle.

In a further embodiment, the reference fuel temperature is determined based on tables or characteristic diagrams.

In a further embodiment, the reference fuel temperature is determined at a start of the motor vehicle.

In a further embodiment, the method is used to measure a fuel temperature in the rail or injector forward flow of an injection system of a diesel engine.

BRIEF DESCRIPTION OF THE DRAWINGS

Example embodiments are discussed below with reference to the figures, in which.

DETAILED DESCRIPTION

Figure 1:
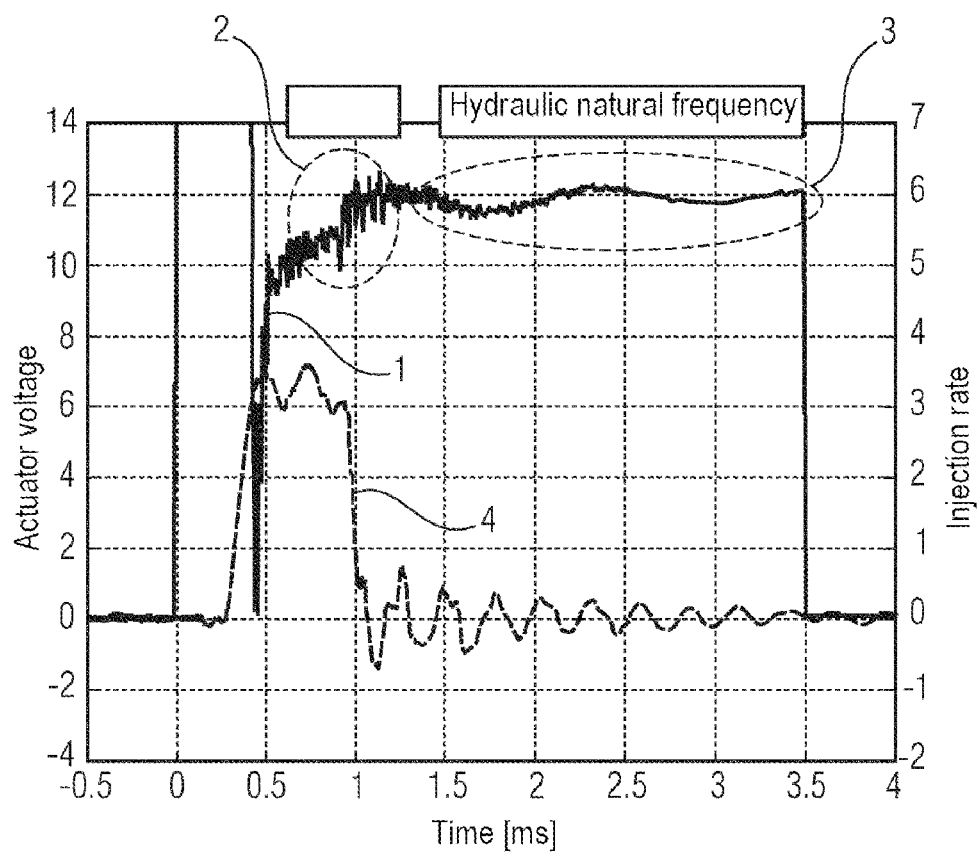
FIG. 1 shows a diagram which represents the profile of the actuator voltage and the injection rate plotted over time.

One embodiment of the invention provides a method including the following steps:

determining a reference fuel temperature with an associated reference natural frequency of the enclosed high-pressure volume of fuel of the fuel injection system, carrying out injection and discharging of the piezo actuator after the ending of the injection in such a way that the servo valve can close but a non-positive connection remains between the piezo actuator and the servo valve, maintaining this state of reduced charge and determining the natural frequency of the enclosed high-pressure volume of fuel, and comparing the determined natural frequency with the reference natural frequency and determining the fuel temperature from the comparison result.

Embodiments of the method allow for the determination of the fuel temperature in the high-pressure zone, in particular in the rail or in the injector forward flow, of a fuel injection system, without requiring a temperature sensor for this purpose. The fuel injection system in question here, in particular that of a diesel engine, comprises at least one injector which is operated by means of a servo valve which is actuated by means of a piezo actuator. In the case of such a servo injector, the opening of the needle is initiated by the actuation of a servo valve. In this context, a piezo actuator is charged electrically until its change in length is sufficient to close the air gap between the actuator and the valve head of the servo valve, and to lift the valve head out of its seat. The pressure present in a control space can then decrease via an outflow throttle and the servo valve into a return flow. The disequilibrium of forces which is now present at the injector needle causes the latter to lift out of the seat. Injection into the combustion chamber begins.

If the piezo actuator is now discharged, it shortens again and the servo valve is closed. The pressure in the control space can increase and the needle closes. The injection is ended.

If the piezo actuator in such a fuel injection system with a servo valve is now discharged to such an extent that, although the servo valve can close, a non-positive connection remains between the servo valve (the valve head thereof) and the piezo actuator, the direct piezo effect can be used to measure the pressure in the control space. In this way, the time of the closing of the needle can be detected.

According to the invention, such a state of reduced charge of the piezo actuator is then used to determine the fuel temperature in the high-pressure zone of the injection system. The state of reduced charge of the piezo actuator is maintained over a short time period, for example several milliseconds, after the end of the injection and the pump delivery, with the result that oscillation occurs in the actuator voltage. This oscillation in the pressure corresponds to the natural frequency of the enclosed high-pressure volume of the injection system.

If the fuel temperature in the system changes, the density of the fuel and consequently also its natural frequency changes. Conclusions can therefore be drawn about the prevailing fuel temperature by measuring the frequencies which occur (the natural frequency and the changes therein).

According to the invention, the temperature or the change in temperature of the fuel in the high-pressure zone (rail) of the injection system can therefore be measured without additional sensors.

In particular, with the method according to the invention the procedure here is such that at first a reference fuel temperature with an associated reference natural frequency of the enclosed high-pressure volume of fuel of the fuel injection system is determined. Since with the method according to the invention only changes in temperature can be measured, firstly a reference temperature must be determined and recorded. Such a reference fuel temperature can be stored together with an associated reference natural frequency. On the basis of this reference temperature with a reference natural frequency it is then possible to infer the change in temperature of the fuel while taking into account the respective rail pressure by measuring the hydraulic natural frequency. In this context, the determined (measured) natural frequency is compared with the reference natural frequency. The change in the fuel temperature or the fuel temperature itself is determined from the comparison result.

The natural frequency of the enclosed high-pressure volume of fuel is determined here specifically from the oscillation of the post-stroke voltage of the piezo actuator.

With the method according to the invention it is possible to obtain a series of advantages. As a result, one or more temperature sensors can be replaced, with the result that the costs for such a fuel injection system can be reduced. If a temperature sensor is present which supplies a temperature value, the plausibility of this sensor value can be checked by means of the method according to the invention. In the case of a defect in the temperature sensor, an equivalent value can be supplied by means of the method according to the invention. The plausibility of a value originating from modeling implemented in the software can also be checked. In addition, a tuning protection can be implemented (the temperature measured by means of the method according to the invention serves for checking the plausibility of the rail pressure here).

In the method according to the invention, the change in temperature of the fuel is inferred on the basis of the reference temperature or reference natural frequency by measuring the hydraulic natural frequency after an injection process, as explained above. This is preferably done by taking into account the respective rail pressure.

In the method according to the invention, the reference fuel temperature is preferably determined with at least one temperature sensor of the motor vehicle. In this method variant, a reference temperature can be determined from one or more temperature sensors, for example an external temperature sensor, which are present, and stored with an associated reference natural frequency. In this context the reference fuel temperature is preferably determined at the start of the motor vehicle, with the result that an updated reference fuel temperature or reference natural frequency is available in each case for the method according to the invention. In another method variant, the reference fuel temperature with the associated reference natural frequency is obtained from tables and/or characteristic diagrams and made available for the method according to the invention.

The method according to the invention is preferably used to measure the temperature in the rail or injector forward flow of an injection system of a diesel engine, and can be implemented by a control system of the motor vehicle including any suitable processing and memory devices for executing the method.

In the following exemplary embodiment, the fuel temperature in the high-pressure zone of a fuel injection system of a diesel engine is determined. The fuel injection system has at least one injector which is operated by means of a servo valve which is actuated by means of a piezo actuator. The method of functioning of such an injection system is known and is therefore not described any further here in detail.

After an injection process has been carried out with the at least one injector, the associated piezo actuator is discharged. However, the piezo actuator is initially discharged only to such an extent that, although the servo valve can close, a non-positive connection remains between the valve head of the servo valve and the piezo actuator. This state of reduced charge is maintained for several milliseconds after the ending of the injection and the pump delivery, with the result that corresponding oscillation occurs in the actuator voltage. This behavior is illustrated in FIG. 1. In the diagram in FIG. 1, the actuator voltage is specified on the left and the injection rate on the right on the ordinate. The time is specified on the abscissa. The profile of the actuator voltage is characterized by the curve 1. The needle closing point is represented by 2. As mentioned, a state of reduced charge is then maintained over several milliseconds, with the result that corresponding oscillation of the voltage occurs here, which is characterized by 3 and which corresponds to the hydraulic natural frequency of the enclosed fuel volume.

Figure 2:
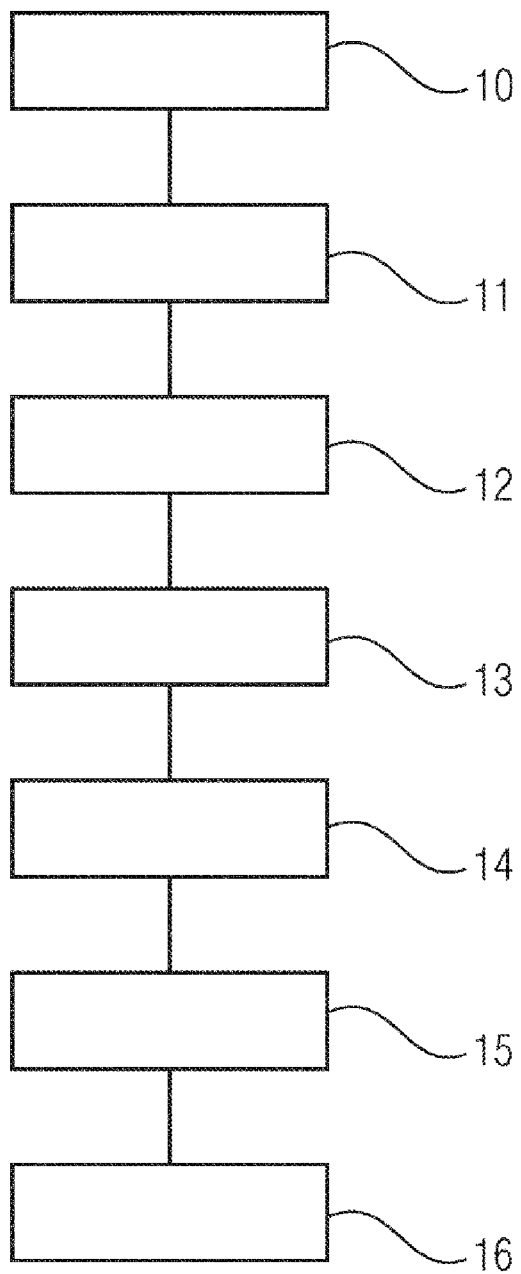
FIG. 2 shows a schematic flowchart of the individual steps of the method for determining the fuel temperature.

The profile of the injection rate is represented by the curve 4. In the method according to the invention, the natural frequency of the enclosed high-pressure volume of fuel is then measured. The fuel temperature can then be ascertained therefrom. In particular, the procedure here is as illustrated in the flowchart in FIG. 2.

Since only changes in temperature can be measured in the way described above, at the start of the vehicle a reference temperature must firstly be recorded. According to step 10, a reference temperature of the fuel is determined from one or more temperature sensors which are present and is stored with an associated reference natural frequency. The associated reference natural frequency for this reference temperature can be determined from corresponding tables or characteristic diagrams. In the subsequent step 11, the reference temperature is stored with an associated natural frequency.

A customary injection process then takes place, said injection process being characterized by step 12. After the servo valve has been closed and a non-positive connection has been maintained between the valve and the piezo actuator with a reduced charge of the piezo actuator according to step 13, the associated natural frequency is determined from the oscillation of pressure of the actuator voltage (post-stroke voltage) (step 14). The relationship between the actuator voltage and the natural frequency, which is known, can be used here as a basis for the corresponding computing operations.

In step 15, the determined natural frequency is compared with the stored reference natural frequency. In this context, the respective rail pressure is taken into account. The change in the fuel temperature compared to the reference temperature can be determined from the corresponding change in the natural frequency or difference between the natural frequencies by using tables or characteristic diagrams. The corresponding fuel temperature value can be derived therefrom (step 16).

What is claimed is:

1. A method for determining the fuel temperature in the high-pressure zone of a fuel injection system of a motor vehicle having at least one injector operated by a servo valve that is actuated by a piezo actuator, the method comprising:
   determining a reference fuel temperature having an associated reference natural frequency of the enclosed high-pressure volume of fuel of the fuel injection system,
   performing an injection, and after the injection, discharging the piezo actuator to a state of reduced charge in which the servo valve is allowed to close but a non-positive connection remains between the piezo actuator and the servo valve,
   maintaining the state of reduced charge and determining a natural frequency of the enclosed high-pressure volume of fuel,
   comparing the determined natural frequency with the reference natural frequency, and
   determining a fuel temperature based on the comparison.

2. The method of claim 1, wherein the natural frequency of the enclosed high-pressure volume of fuel is determined from the oscillation of the post-stroke voltage of the piezo actuator.

3. The method of claim 1, wherein the reference fuel temperature is determined using at least one temperature sensor of the motor vehicle.

4. The method of claim 1, wherein the reference fuel temperature is determined based on tables or characteristic diagrams.

5. The method of claim 1, wherein the reference fuel temperature is determined at a start of the motor vehicle.

6. The method of claim 1, wherein the method is used to measure a fuel temperature in the rail or injector forward flow of an injection system of a diesel engine.

7. A control system for determining the fuel temperature in the high-pressure zone of a fuel injection system of a motor vehicle having at least one injector operated by a servo valve that is actuated by a piezo actuator, the control system configured to:
   determine a reference fuel temperature having an associated reference natural frequency of the enclosed high-pressure volume of fuel of the fuel injection system,
   perform an injection, and after the injection, discharging the piezo actuator to a state of reduced charge in which the servo valve is allowed to close but a non-positive connection remains between the piezo actuator and the servo valve,
   maintain the state of reduced charge and determining a natural frequency of the enclosed high-pressure volume of fuel,
   compare the determined natural frequency with the reference natural frequency, and
   determine a fuel temperature based on the comparison.

8. The control system of claim 7, wherein the natural frequency of the enclosed high-pressure volume of fuel is determined from the oscillation of the post-stroke voltage of the piezo actuator.

9. The control system of claim 7, wherein the reference fuel temperature is determined using at least one temperature sensor of the motor vehicle.

10. The control system of claim 7, wherein the reference fuel temperature is determined based on tables or characteristic diagrams.

11. The control system of claim 7, wherein the reference fuel temperature is determined at a start of the motor vehicle.

* * * * *